(12) United States Patent
Fu et al.

(10) Patent No.: US 8,552,074 B2
(45) Date of Patent: Oct. 8, 2013

(54) PROCESS FOR PREPARING METHANOL, DIMETHYL ETHER, AND LOW CARBON OLEFINS FROM SYNGAS

(75) Inventors: Qiang Fu, Beijing (CN); Xiaoxin Zhang, Beijing (CN); Yibin Luo, Beijing (CN); Xuhong Mu, Beijing (CN); Baoning Zong, Beijing (CN)

(73) Assignees: China Petroleum & Chemical Corporation, Beijing (CH); Research Institute of Petroleum Processing, SINOPEC, Beijing (CN)

( * ) Notice: Subject to any disclaimer, the term of this patent is extended or adjusted under 35 U.S.C. 154(b) by 225 days.

(21) Appl. No.: 13/139,513

(22) PCT Filed: Dec. 15, 2009

(86) PCT No.: PCT/CN2009/001452
§ 371 (c)(1),
(2), (4) Date: Jul. 20, 2011

(87) PCT Pub. No.: WO2010/069133
PCT Pub. Date: Jun. 24, 2010

(65) Prior Publication Data
US 2012/0083539 A1  Apr. 5, 2012

(30) Foreign Application Priority Data
Dec. 18, 2008  (CN) .......................... 2008 1 0240261

(51) Int. Cl.
*C07C 27/00* (2006.01)
(52) U.S. Cl.
USPC ............ 518/714; 518/700; 518/713; 518/715
(58) Field of Classification Search
USPC .................................. 518/700, 713, 714, 715
See application file for complete search history.

(56) References Cited

U.S. PATENT DOCUMENTS

| 4,366,260 A | 12/1982 | Wainwright et al. |
| 4,436,833 A | 3/1984 | Broecker et al. |
| 5,389,689 A | 2/1995 | Fujimoto et al. |
| 2007/0244000 A1* | 10/2007 | Molinier et al. .............. 502/300 |

FOREIGN PATENT DOCUMENTS

| CN | 1065026 A | 10/1992 |
| CN | 1390640 A | 1/2003 |
| JP | 59102444 A | 6/1984 |
| JP | 60087233 A | 5/1985 |

OTHER PUBLICATIONS

Chemical Abstract CN 1073726, Jun. 1993.*
A. Yokoyama, H. Komiyama, H. Inoue, T. Masumoto, H.M. Kimura, The hydrogenation of carbon monoxide by amorphous ribbons, Journal of Catalysis, vol. 68, Issue 2, Apr. 1981, pp. 355-361.

* cited by examiner

*Primary Examiner* — Jafar Parsa
(74) *Attorney, Agent, or Firm* — Novick, Kim & Lee PLLC; Allen Xue (57) ABSTRACT

The present invention provides a process for preparing methanol, dimethyl ether, and low carbon olefins from syngas, wherein the process comprises the step of contacting syngas with a catalyst under the conditions for converting the syngas into methanol, dimethyl ether, and low carbon olefins, characterized in that, the catalyst contains an amorphous alloy consisting of components M and X wherein the component X represents an element B and/or P, the component M represents two or more elements selected from Group IIIA, IVA, VA, IB, IIB, IVB, VB, VIB, VIIB, VIII and Lanthanide series of the Periodic Table of Elements. According to the present process, the syngas can be converted into methanol, dimethyl ether, and low carbon olefins in a high CO conversion, a high selectivity of the target product, and high carbon availability.

17 Claims, 3 Drawing Sheets

Figure 1: XRD spectrum ((1)Catalyst of Example 1, (2)Catalyst of Comparative example 1, (3)Catalyst of Comparative example 2)

Figure 2: XRD spectrum ((1)Catalyst of Example 5, (2)Catalyst of Example 6)

Figure 3: XRD spectrum((1)Catalyst of Example 7, (2)Catalyst of Comparative example 3)

PROCESS FOR PREPARING METHANOL, DIMETHYL ETHER, AND LOW CARBON OLEFINS FROM SYNGAS

THE TECHNICAL FIELD

The present invention relates to a process for preparing methanol, dimethyl ether, and low carbon olefins from syngas.

BACKGROUND

The synthesis of methanol is an important chemical engineering process. Currently, the Cu—Zn—Al catalyst is the main component of the widely-used industrial catalyst for the synthesis of methanol at a low pressure. It is generally prepared by a co-precipitation method, and the resultant catalyst is a mixture of Cu, Zn, and Al oxides. For example, U.S. Pat. No. 4,436,833 discloses a co-precipitation method comprising mixing a solution of Cu, Zn, and Al nitrates with sodium carbonate as a precipitation agent to form a carbonate precipitate, washing off the sodium ions with distilled water, and drying and calcining to produce a mixture of Cu, Zn, and Al oxides for catalytic synthesis of methanol. The catalyst, however, has the disadvantage that it is difficult to wash off the sodium ions and control the temperature during the reduction process, resulting in a significant decrease of the catalytic activities.

U.S. Pat. No. 4,366,260 discloses a method for preparing methanol, or mixtures of methanol and dimethyl ether. The catalyst used in the method is a Raney Cu catalyst which is prepared from an alloy containing from 35 to 60% by weight of aluminum, 0.1 to 25% by weight of zinc, and the remainder being substantially all copper. It is known to those skilled in the art that the alloy of the Raney Cu catalyst is a crystalline alloy. The methanol yield by means of the catalyst under the reaction conditions suitable for preparing methanol from syngas is relative low (10.9% only).

Dimethyl ether (DME) is a widely interesting, environmentally friendly, super-clean replacement product for civilian and automobile fuels. There are mainly two production methods of dimethyl ether, i.e. one-step method and two-steps method. The two-steps method resides in synthesizing methanol from syngas, and then dehydrating to produce dimethyl ether. The one-step method means that dimethyl ether is synthesized from the feedstock syngas in one step, and comprises three main reaction steps which are relevant from each other and proceed sequentially:

$$CO + 2H_2 \rightarrow CH_3OH \quad (1)$$

$$2CH_3OH \rightarrow CH_3OCH_3 + H_2O \quad (2)$$

$$CO + H_2O \rightarrow CO_2 + H_2 \quad (3)$$

Although all three reactions are reversible, the whole reaction procedure can proceed in a state which deviates from the thermodynamic equilibrium since products from each of the reaction step are consumed in the next reaction. Therefore, compared with a single methanol synthesis reaction, the conditions for the dimethyl ether synthesis reaction process directly from syngas are much milder, and the one-pass CO conversion is much higher. Compared with the two-steps method, the one-step method for dimethyl ether synthesis is carried out without an intermediate procedure for the methanol synthesis, and it has the advantages of simpler procedure, less devices, and lower investment and operation cost. Therefore, the production cost for dimethyl ether is decreased and the economic benefit is increased. Thus, the one-step method for dimethyl ether synthesis is of great interest in the research & development in many countries. The catalyst system for the one-step synthesis of dimethyl ether is generally a physical mixture of a methanol synthesis catalyst and a methanol dehydration catalyst. The industrial catalyst for methanol synthesis generally contains one or more of Cu, Zn, Al and Cr, and it is well known for those skilled in the art that the catalyst is a crystalline alloy, whereas the methanol dehydration catalyst is generally chosen from solid acidic materials.

U.S. Pat. No. 5,389,689 discloses a preparation method of the catalyst for producing dimethyl ether in one-step, comprising pulverizing the mixture containing zinc oxide, copper oxide or chromic oxide, and aluminum oxide to particle sizes of from about 0.1 to 20 μm, pressing under a pressure of 100-500 kg/cm$^3$ to adhere the oxides together, then suspending in the solvent and again pulverizing the slurry formed therefrom to obtain the catalyst. Under the reaction conditions comprising a H$_2$/CO molar ratio of 1, a reaction temperature of 280° C., and a reaction pressure of 3 MPa, the CO conversion is 60.1%, the yield of dimethyl ether is 42.8%, and the yield of CO$_2$ is 14.4%. The catalyst for producing dimethyl ether has a low activity, the temperature desired is relatively high, and the CO conversion is relatively low. Moreover, about one third of CO is converted into useless CO$_2$ due to the low hydrogenation activity of the catalyst. Other side reactions occur during the reaction procedure, resulting in carbon availability of generally less than 60%. The reaction process is less cost-effective.

Low carbon olefins (light olefins) which mainly refer to ethylene and propylene are very important raw materials for the chemical engineering. Presently, more than 90% of low carbon olefins are produced from the cracking of light oils. The supply of low carbon olefins is unable to meet the demand in the market. In view of the economic continuous development, and increasing deficiency of the petroleum source, it is absolutely necessary to produce low carbon olefins from a replacement source. The technique for directly preparing olefins from syngas originates from the traditional F-T synthesis. Since the carbon number of the product obtained from the F-T synthesis catalyst follows the S-T distribution law, the selectivity of low carbon olefins is low. The preparation of catalysts having a high activity and selectivity is of great interest in the current research field.

CN1065026A discloses a catalyst for preparing ethylene from syngas. The catalyst comprises one oxide of the element selected from Si, Al, Ti, Nb, and Hf, one or two oxides of the element selected from Nb, Y, Ga, Ge, In, and Tl, one or more oxides of the element selected from Sn, Pb, Sc, La, Pr, Ce, and Nd, and is prepared by a method selected from impregnation, co-precipitation, mechanical mixing, slurry-mixing, a combination of impregnation and co-precipitation, or a combination of mechanical mixing and impregnation. Although the ethylene selectivity can be up to 94% when the catalyst is used in the preparation of ethylene from syngas, the CO conversion is only 15%.

CN1390640A discloses a nano copper catalyst for synthesizing methanol or dimethyl ether, and preparation method thereof. The catalyst consists of metal Cu, ZnO, alumina, etc., wherein the molar ratio among these components is 30-60% Cu:60-30% Zn:10-15% Al. The nano Cu has a size of from 2 to 10 nm and is highly dispersed on a complex carrier of ZnO-alumina. The catalyst is prepared by forming a co-precipitate slurry containing Cu, Zn, and Al compounds by a co-precipitation method; and then directly reacting the co-precipitate slurry with a reducing agent to reduce Cu; the reducing agent is remained in the solution after being oxidized by $Cu^{2+}$, and the $Cu^{2+}$ compound aggregate in a nanometer size is reduced and then the resultant crystalline elemental Cu in a nanometer size is dispersed on the carrier; then the precipitate is filtered by suction, washed, and dried under vacuum; finally the product is tableted, or calcined under an inertia gas or vacuum at 250-400° C. to obtain the catalyst. However, the yield of methanol in the methanol or dimethyl ether synthesis process using the catalyst is relatively low. For example, the yield of methanol at 240° C. is only 6.5%. Moreover, the catalyst has to be subjected to a complex and time-consuming pre-reduction process before being used in the synthesis process.

SUMMARY OF INVENTION

The present invention aims to overcome the disadvantages of low CO conversion, target product selectivity, and carbon availability during the prior preparation process of methanol, dimethyl ether and/or low carbon olefins from syngas, and to provide a preparation process of methanol, dimethyl ether and/or low carbon olefins from syngas which has a high CO conversion, target product selectivity, and carbon availability.

The present invention provides a process for preparing methanol, dimethyl ether, and low carbon olefins from syngas, wherein the process comprises the step of contacting syngas with a catalyst under the conditions for converting the syngas into methanol, dimethyl ether, and low carbon olefins, characterized in that, the catalyst contains an amorphous alloy consisting of components M and X wherein the component X represents an element B (boron) and/or P (phosphorus), the component M represents two or more elements selected from Group IIIA, IVA, VA, IB, IIB, IVB, VB, VIB, VIIB, VIII and Lanthanide series of the Periodic Table of Elements.

In the inventive process for preparing methanol, dimethyl ether, and low carbon olefins from syngas, the use of the catalyst containing an amorphous alloy consisting of component B and/or P and two or more elements selected from Group IIIA, IVA, VA, IB, IIB, IVB, VB, VIB, VIIB, VIII and Lanthanide series of the Periodic Table of Elements results in a very high CO conversion, target product selectivity, and carbon availability.

DETAILED DESCRIPTION OF THE EMBODIMENT

The term "syngas" (synthesis gas) means a feedstock gas mixture comprising CO and $H_2$ as the main components. The syngas is generally obtained from solid raw materials (e.g. coal, coke), liquid raw materials (e.g. light oils, heavy oils), and gaseous raw materials (e.g. natural gases, oil field gases). For example, the syngas can be one or more gases selected from coke oven gases, liquefied gases, water gases, semi-water gases, natural gases, and oil field gases.

The present invention provides a process for preparing methanol, dimethyl ether, and/or low carbon olefins from syngas, wherein the process comprises the step of contacting syngas with a catalyst under the conditions for converting the syngas into methanol, dimethyl ether, and/or low carbon olefins, characterized in that, the catalyst contains an amorphous alloy consisting of components M and X wherein the component X represents an element B and/or P, the component M represents two or more elements selected from Group IIIA, IVA, VA, IB, IIB, IVB, VB, VIB, VIIB, VIII and Lanthanide series of the Periodic Table of Elements.

According to process provided by the present invention, preferably, the molar ratio between the component M and component X in the amorphous alloy (i.e. M:X) is equal to or greater than 0.01, more preferably equal to or greater than 0.05, most preferably equal to or greater than 0.2, but equal to or lower than 15, more preferably equal to or lower than 10, most preferably equal to or lower than 5.

According to process provided by the present invention, preferably, said component M is two or more elements selected from Lanthanide series, and the third, fourth and fifth rows of Group IIIA, IVA, VA, IB, IIB, IVB, VB, VIB, VIIB, and VIII of the Periodic Table of Elements, more preferably two or more elements selected from Cu, Zn, V, Cr, Mn, Fe, Co, Ni, Zr, Mo, Sn and La. In some preferred embodiments, said component M comprises Cu. In some preferred embodiments, said component M comprises Cu and Zn. In some preferred embodiments, component M excludes Al.

According to process provided by the present invention, the amorphous alloy represented by M-X can be M-P, M-B, or M-B—P amorphous alloy. In case of M-B—P, the molar ratio between B and P is preferably from 0.05 to 3. The components in said amorphous alloy can be present in a pure amorphous form, or in a form of a mixture of amorphous alloys and microcrystalline and/or crystalline alloys (i.e. a part of the alloy is in an amorphous form) wherein the microcrystalline and crystalline alloys are present in an total amount of preferably less than 30 wt. % by the total weight of the alloy. For example, said M-B—P amorphous alloy can be present in a multi-crystalline form wherein either the M-B—P amorphous alloys or the mixture of the M-P and M-B amorphous alloy coexists with microcrystalline and/or crystalline alloys thereof (i.e. a part of the alloy is in an amorphous form), and the microcrystalline and crystalline alloys are present in an total amount of preferably less than 30 wt. % by the total weight of the alloy.

According to process provided by the present invention, the preparation method of the amorphous alloy comprises, e.g. the steps of contacting and reacting an aqueous solution containing M ion with an aqueous solution containing H2PO2- ion and/or BH4- ion, wherein M represents two or more elements selected from Group IIIA, IVA, VA, IB, IIB, IVB, VB, VIB, VIIB, VIII and Lanthanide series of the Periodic Table of Elements. The aqueous solution of P and/or B, as a reducing agent, is preferably added slowly or dropwise to the reaction.

In the preparation method of the above amorphous alloy, preferably, the ratio between the molar amount of said M ion and the total molar amount of $H_2PO_2^-$ ion and $BH_4^-$ ion is from 0.05 to 5.

In the preparation method of the above amorphous alloy, preferably, the molar concentration of the M ion in said aqueous solution containing M ion is 0.01-5.0 mol/L; the molar concentration of the $H_2PO_2^-$ ion in said aqueous solution containing $H_2PO_2^-$ ion is 0.01-5.0 mol/L; the molar concentration of the $BH_4^-$ ion in said aqueous solution containing $BH_4^-$ ion is 0.01-5.0 mol/L.

In the preparation method of the above M-P or M-B amorphous alloy, the aqueous solution containing $H_2PO_2^-$ ion or the aqueous solution containing $BH_4^-$ ion is contacted and reacted with the aqueous solution containing M ion. In the preparation method of the above M-B—P amorphous alloy, an amount (e.g. a relative low amount) of the aqueous solution containing $H_2PO_2^-$ ion in a certain concentration (e.g. a relative low concentration) is mixed homogeneously with the aqueous solution containing M ion to obtain a clear solution, and then the aqueous solution containing $BH_4^-$ ion is added dropwise to the clear solution to conduct the reaction.

In the preparation method of the above amorphous alloy, the contact and reaction are generally conducted at a room temperature, and a precipitate is formed rapidly. Then the precipitate is washed and dried (preferably naturally dried).

The presence of the amorphous alloy in the product obtained by the above method can be identified by the X-ray powder diffraction (XRD) method. A broad diffraction peak in the XRD spectrum means that the alloy is in a form of amorphous alloy.

According to process provided by the present invention, said catalyst preferably contains a carrier into or onto which the amorphous alloy is dispersed or loaded. Preferably and based on the total weight of the catalyst, the amount of the amorphous alloy is 3-90 wt. %, more preferably 10-60 wt. %, and the amount of the carrier is 10-97 wt. %, more preferably 40-90 wt. %.

According to process provided by the present invention, the carrier can be selected from those frequently used in catalysts in the art, e.g. one or more of non-oxidative porous inorganic oxides, molecular sieves, active carbons, clays, phosphates (e.g. aluminum phosphate), sulfates (e.g. magnesium sulfate), and metal halides (e.g $FeCl_3$, $SnCl_4$, $ZnCl_2$).

The non-oxidative porous inorganic oxides are well known to those skilled in the art, and can be one or more selected from alumina, silica, alumina-silica, zirconia, titania, zinc oxide, boron oxide, and alkaline earth metal oxide. The non-oxidative porous inorganic oxides are commercially available, or can be prepared by a co-precipitation method which is well known to those skilled in the art.

Said molecular sieves are well known to those skilled in the art, e.g. silicon-aluminum molecular sieves, hetero-atom molecular sieves.

Said clays are well known to those skilled in the art, e.g. kaolin, halloysite, montmorillonite, diatomaceous earth, halloysite, saponite, rectorite, sepiolite, attapulgite, hydrotalcite, bentonite, more preferably kaolin, montmorillonite.

As known to those skilled in the art, a heteropolyacid, e.g. phosphotungstic acid and/or phosphomolybdic acid can be loaded on/in the carrier.

According to process provided by the present invention, preferably, said carrier contains an adjuvant which is loaded on/in the carrier and selected from one or more elements or oxides thereof of Group IA, IIA, IIIA, IVA, VA, IB, IIB, IVB, VIII, and Lanthanide series of the Periodic Table of Elements. More preferably, said adjuvant is one or more elements or oxides thereof selected from Lanthanide series, and the third, fourth and fifth rows of Group IA, IIA, IIIA, IVA, VA, IB, IIB, IVB, and VIII of the Periodic Table of Elements, even more preferably one or more elements or oxides selected from K, Ca, Mg, Ga, Sn, P, Cu, Zn, Zr, Fe, and La. Loading the adjuvant on/in the carrier can increase the activity and selectivity of the reaction.

According to process provided by the present invention, preferably and based on the weight of the carrier, the amount of the adjuvant is 0.5-40 wt. %. Said adjuvant can be loaded in/on a part of or the entire carrier by an ion-exchange method, impregnation method, kneading method, or precipitation method which is well known to those skilled in the art.

In the ion exchange method, e.g. a carrier adhered with $H^+$ and/or $Na^+$ on the surface and an aqueous solution containing ions of the adjuvant element can be homogeneously mixed, heated to 80° C. and stirred for 1 hr, then filtered, and the filtration product is repeatedly washed with distilled water and dried at a temperature of 110° C.

In the impregnation method, e.g. a carrier can be impregnated in an aqueous solution containing ions of the adjuvant element at 60° C. for 8 hrs, dried at 110° C., and then calcined at 550° C. for 2 hrs.

In the precipitation method, e.g. a carrier and an aqueous solution containing ions of the adjuvant element can be mixed homogeneously, then a precipitation agent e.g. sodium carbonate is added to produce a precipitate, and the resultant precipitate is filtered, washed repeated with distilled water, dried at 110° C., and then calcined at 550° C. for 2 hrs.

The catalyst compounded from the amorphous alloy and carrier has a superior catalytic activity, selectivity of the target product, poisoning resistance, and repeatability of the catalyst property. Meanwhile, the stability of the catalyst is superior too. The regeneration period of the catalyst can be as long as 3 months or longer. Moreover, the catalyst is easily usable in the reaction. A reduction and activation step for a catalyst, which otherwise should be carried out prior to the reaction in the prior art and often is complex, difficult and time-consuming, can be omitted in the present process. The preparation method of the inventive catalyst is simple, easily operable, and easy to be scaled up in the industry.

In the preferable case that the amorphous alloy is loaded in/on the carrier, the catalyst can be a homogeneous mixture of carriers in which a part of the carriers have been loaded with the amorphous alloy but the other carriers have not been loaded. These two parts of carriers can be the same or different each other. In such way, the catalytic property can be further improved.

The catalyst can be prepared by the following methods: 1) mechanically mixing the amorphous alloy and the carrier to obtain the catalyst in which the amorphous alloy is dispersed into the carrier; 2) using an impregnation-reduction or reduction-impregnation method to directly impregnate the amorphous alloy onto the carrier to obtain the catalyst in which the amorphous alloy is loaded onto the carrier; or 3) using a co-precipitation method to directly deposit the amorphous alloy onto the carrier to obtain the catalyst in which the amorphous alloy is loaded onto the carrier; or any combination of said methods 1)-3).

The method for mechanically mixing the amorphous alloy and the carrier is well known to those skilled in the art. The amorphous alloy and the carrier can be compounded by a mechanical mixing method without any other component, or by adding an adhesive prior to the mechanical mixing. Said adhesive can be silica sol, alumina sol or mixture thereof.

As well known to those skilled in the art, the amorphous alloy can be impregnated onto the carrier by an impregnation-reduction or reduction-impregnation method. For example, said method can be conducted as follows.

The impregnation-reduction method comprises the steps of impregnating the carrier in an aqueous solution containing M ion, then drying the impregnated carrier at a temperature of 100-130° C., calcining at 300-900° C. for 1-10 hrs, and repeating the impregnation process one or more times if necessary; then contacting the calcined carrier with the reducing agent solution containing $H_2PO_2^-$ ion and/or $BH_4^-$ ion for 1-4 hrs, subsequently filtering and drying at a temperature below the crystallization temperature of the metals in the amorphous alloy.

The reduction-impregnation method comprises the steps of simultaneously or separately impregnating the carrier in the reducing agent solution containing $H_2PO_2^-$ ion and/or $BH_4^-$ ion, subsequently filtering and drying, and repeating the impregnation process one or more times if necessary; adding an aqueous solution containing M ion into the obtained carrier under stirring in an ice-water bath, reacting for 1 to 4 hrs;

stirring for further 10-60 minutes after the reaction is finished, filtering and drying at a temperature below the crystallization temperature of the metals in the amorphous alloy.

The presence of the amorphous alloy in the catalyst obtained by the above method can be identified by the XRD method. A broad diffraction peak in the XRD spectrum means that the M-P, M-B, or M-B—P alloy loaded on the carrier in the catalyst is in a form of amorphous alloy.

The co-precipitation method for depositing the amorphous alloy onto the carrier is well known to those skilled in the art. For example, said method can be conducted as follows:

The carrier is dispersed into an aqueous or organic solution containing M ion to obtain a suspension, wherein the concentration of the M ion (e.g. a relatively low concentration) should be chosen to achieve the suspension state when mixed with the carrier, rather than a precipitate state; NaOH is added into the reducing agent solution(s) containing $H_2PO_2^-$ ion or $BH_4^-$ ion separately to adjust the pH to 7-11; preferably under air or nitrogen atmosphere, the above-mentioned pH-adjusted reducing agent solution(s) containing $H_2PO_2^-$ ion and/or $BH_4^-$ ion is added dropwise into the above-mentioned suspension to co-precipitate them. During the co-precipitation process, the metal M is reduced and simultaneously slowly separated out on the carrier surface, and finally deposits on the carrier surface in an amorphous form of M-B, M-P or M-B—P alloy due to the slow reduction process and the barrier function of the reducing agent B or P atom. Subsequently, an optional washing and drying step at a temperature below the crystallization temperature of the metals in the amorphous alloy is conducted to obtain the catalyst.

The presence of the amorphous alloy in the catalyst obtained by the above method can also be identified by the XRD method. A broad diffraction peak in the XRD spectrum means that the M-P, M-B, or M-B—P alloy loaded on the carrier in the catalyst is in a form of amorphous alloy.

In the above impregnation-reduction, reduction-impregnation, and co-precipitation methods for preparing the inventive catalyst, as well as the method for preparing the amorphous alloy, the aqueous solution containing M ion can be obtained by dissolving in water one or more substances selected from the water-soluble chloride, sulfate, nitrate or acetate salt of M ion. The molar concentration of M ion in said aqueous solution containing M ion can be 0.01-5.0 mol/L; the compound containing $H_2PO_2^-$ ion which can be used in above methods can be selected from $KH_2PO_2$ or $NaH_2PO_2$, which can carry crystalline water or not, and the molar concentration of $H_2PO_2^-$ ion in the solution containing the $H_2PO_2^-$ ion can be 0.01-5.0 mol/L; the compound containing $BH_4^-$ ion which can be used in above methods can be selected from $KBH_4$ or $NaBH_4$, and the molar concentration of $BH_4^-$ ion in the solution containing the $BH_4^-$ ion can be 0.01-5.0 mol/L.

After loading the amorphous alloy onto/into the carrier by the impregnation-reduction, reduction-impregnation, or co-precipitation method, it is preferable to mechanically mixing the carrier loaded with the amorphous alloy and the un-loaded carrier. The mechanical mixing method in this regard is same to the above-mentioned mechanical mixing method.

The composition of the catalyst is determined by the X-ray fluorescence spectroscopy (XRFS). The experimental instrument used is the X-ray fluorescence spectrometer 3271E type from Rigaku Industrial Corporation. A rhodium target, an excitation voltage of 50 kV, and an excitation current of 50 mA are employed in the experiment; the spectral line intensity of each element is detected by a scintillation counter and a proportional counter to perform a quantitative or semi-quantitative analysis.

According to process provided by the present invention, preferably, the conditions for converting the syngas into methanol, dimethyl ether, and low carbon olefins comprise a reaction temperature of 200-400° C., a reaction pressure of 0.5-6 MPa, a space velocity of the syngas feedstock of 1000-10000 mL/g·h, and a molar ratio between $H_2$ and CO in the syngas of from 1 to 3.

When the present process aims to obtain methanol and dimethyl ether as the main products, and the low carbon olefins as the byproducts, the reaction temperature is preferably 200-270° C. and the reaction pressure is preferably 1-6 MPa. When the present process aims to obtain the low carbon olefins as the main products, and methanol and dimethyl ether as the byproducts, the reaction temperature is preferably 270-400° C. and the reaction pressure is preferably 0.5-2 MPa.

The reactor can be a fluidized bed reactor or a fixed bed reactor, and the operation process can be carried out in batch mode or continuous mode.

The process according to the present invention preferably comprises a reduction step of the catalyst prior to contacting the catalyst with syngas. The reduction step comprises loading into the reactor the catalyst in an amount of e.g. from 1 to 5 grams, and prior to the reaction, purging the reactor containing the catalyst with a reductive gas at a purging temperature of 130-600° C. for 0.5-1 hr to active the catalyst. The reductive gas may be a mixture of hydrogen in an amount of 1-10 wt. % and inert gas which can be one or more gases selected from nitrogen, helium, and argon.

After the reduction step, the syngas feedstock in a space velocity of 1000-10000 mL/g·h is fed into the reactor at a reaction temperature of 200-400° C. and an operation pressure of 0.5-6 MPa. The syngas can be one or more gases which comprise $H_2$ and CO in a molar ratio of from 1 to 3, e.g. one or more gases selected from coke oven gases, liquefied gases, water gases, semi-water gases, natural gases, and oil field gases.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

Example 1

1. Preparing the Amorphous Alloy

To 300 mL solution of 0.5 mol/L $CuSO_4$ (analytical purity, Cangwu SaintGreen Chemical Co., Ltd, the same below) was added 5 g citric acid (industrial grade) as complexing agent, and added 30 mL solution of 0.05 mol/L $Ga(NO_3)_3$ (analytical purity, Zibo Rongruida Micro Materials Plant). The mixture was stirred sufficiently, to which 30 mL solution of 0.5 mol/L $KBH_4$ (analytical purity, Shanghai Bangcheng Chemical Co., Ltd., the same below) was added dropwise. The reaction proceeded rapidly to form a black precipitate, the supernatant was decanted, the precipitate was washed with water until the filtrate became neutral, then washed with acetone for several times and dried naturally to obtain the product. The molar ratio among the components in the product determined by XRF method was Cu:Ga:B=1:0.01:0.1.

Figure 1:
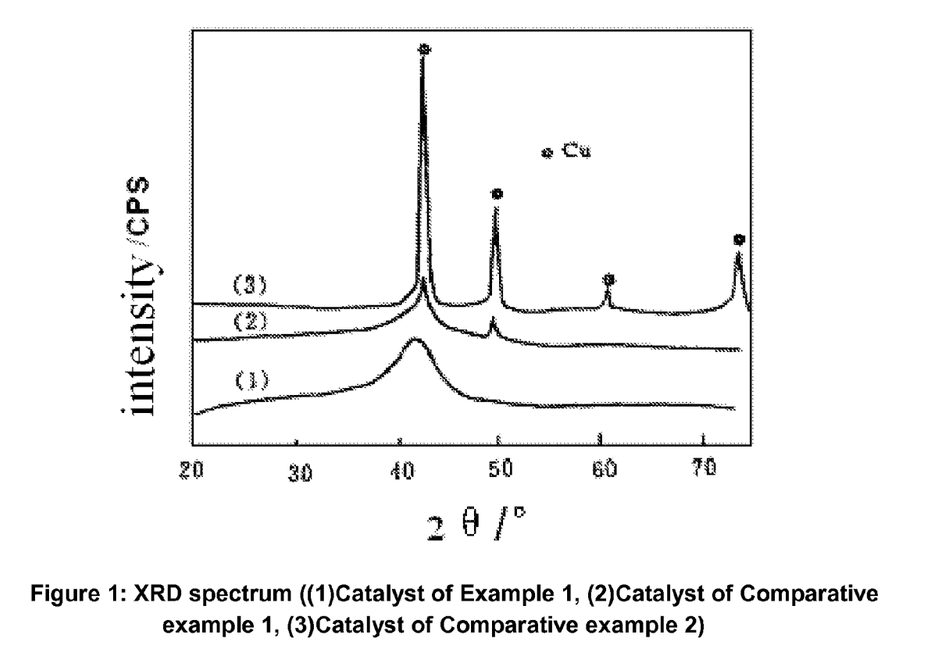
FIGS. 1-3 are the XRD spectrum of the alloys prepared by the inventive examples and comparative examples.

An X-ray powder diffractometer (D/MAX-2500 type X-ray diffractometer from Rigaku Cooperation, Cu Kα ray, a current of 100 mA, the same below) was used to analyze the obtained product by XRD. The resultant XRD spectrum showed that only a broad diffuse peak at 2θ=42° was present (FIG. 1 (1)) which is the typical characteristic of an amorphous alloy. Therefore, the resultant Cu—Ga—B alloy product was an alloy in an amorphous form.

2. Preparing the Carrier of Mixed Oxides 60 g ZnO (industrial purity, the same below), 20 g $SiO_2$ (macroporous silica gel, Qingdao Haiyang Chemical Plant, the same below) and 200 g distilled water were mixed, 130 g aqueous solution of 20 wt. % $ZrOCl_2 \cdot 8H_2O$ (analytical purity, Xinghua Songhe Chemical Reagent Factory), 5 g $MnO_2$ (industrial purity), 49 g aqueous solution of 20 wt. % $CaCl_2$ (industrial purity) and 10 g aqueous solution of 1 wt. % HCl (analytical purity, Beijing Chemical Works, the same below) were simultaneously added dropwise under strongly stirring, and then 50 g aqueous solution of 5 wt. % sodium carbonate (analytical purity, Beijing Chemical Works, the same below) was added dropwise. After the addition was complete, the mixture was stirred for further 1 hr, the resultant precipitate was filtered and washed with distilled water repeatedly until there was no $Cl^-$. The precipitate was dried at 110° C. and then calcined at 550° C. for 2 hrs to obtain 100 g carrier comprising ZnO 60 wt. %, $SiO_2$ 20 wt. %, $ZrO_2$ 10 wt. %, adjuvant $MnO_2$ 5 wt. %, and adjuvant CaO 5 wt. %.

3. Compounding the Catalyst

The amorphous alloy and carrier obtained in above steps were mixed mechanically in a weight ratio of 2:3, tableted, pulverized and screened to particles having sizes of from 20 to 40 meshes. A catalyst was obtained which composition was shown in Table 1.

Example 2

1. Preparing the Amorphous Alloy

Each 20 mL of 0.86 mol/L $CuSO_4$ solution and 0.45 mol/L $Mn(SO_4)_2$ solution (analytical purity, Hunan Coran Chemical Co., LTD) was mixed with 344 mL 0.1 mol/L $NaH_2PO_2$ solution (analytical purity, Lufang Chemical Co., LTD, the same below) and stirred homogeneously. The temperature of the mixture was kept at 30° C. in water bath, and then 13.6 mL solution of 5.0 mol/L $NaBH_4$ (analytical purity, Shanghai Bangcheng Chemical Co., Ltd., the same below) which pH had been adjusted to 12 by NaOH was added therein dropwise and stirred homogeneously. After the addition was complete, the reaction was stirred for further 15 minutes, and then filtered to obtain a black precipitate. The precipitate was washed with water until the filtrate became neutral, then with acetone for several times and dried naturally to obtain the product. The molar ratio among the components in the product determined by XRF method was Cu:Mn:P:B=1:0.52:2:4.

An X-ray powder diffractometer was used to analyze the obtained product by XRD. The resultant XRD spectrum showed that only a broad diffuse peak at 2θ=42° was present (the resultant XRD spectrum being similar to FIG. 1 (1)) which is the typical characteristic of an amorphous alloy. Therefore, the resultant Cu—Mn—P—B alloy product was an alloy in an amorphous form.

2. Preparing the Carrier Containing Active Carbon and Metal Chloride 5 g $FeCl_3$ (analytic purity, Jiangyin Hengye Chemical Engineering Co. Ltd., China, the same below), 5 g $SnCl_4$ (analytic purity, Liaoyang Dingxin Chemical Engineering Co. Ltd., China), 30 g $ZnCl_2$ (industrial purity) and 60 g active carbon powders (Xinsen Tanye Co. Ltd., Shaowu city, Fujian Province, China) were sufficiently kneaded to give 100 g of carrier containing $FeCl_3$ 5 wt. %, $SnCl_4$ 5 wt. %, $ZnCl_2$ 30 wt. %, and active carbon 60 wt. %.

3. Compounding the Catalyst 33 g amorphous alloy obtained in above steps, 100 g carrier obtained in above steps, 12.5 g silica sol (40 wt. %, Sinopec Catalyst Company Qilu filiale) and 25 g alumina sol (20 wt. %, Sinopec Catalyst Company Qilu filiale) were mixed homogeneously, extruded from an extruder, pulverized and screened to particles having sizes of from 20 to 40 meshes, dried under vacuum and at a temperature of 120° C. for 4 hrs to obtain the catalyst which contained 23 wt. % of the amorphous alloy and its composition was shown in Table 1.

Example 3

1. Preparing the Amorphous Alloy

To 60 mL solution of 2.5 mol/L $CuSO_4$ was added 3 g citric acid, and then 60 mL 0.05 mol/L $VCl_2$ solution (analytical purity, Beijing Hengyunzhongyuan Chemical Co., Ltd.). The mixture was stirred sufficiently, then 6 mL solution of 5.0 mol/L $KH_2PO_2$ (analytical purity, Lufang Chemical Co., LTD, the same below) was slowly added therein, the pH of the mixed solution was adjusted to 7 with ammonia water (analytical purity, Beijing Chemical Works, the same below), and 10 mL aqueous solution of 0.01 mol/L $NaBH_4$ was added therein at 20° C. After the reaction was complete, ammonia water was added therein and stirred for 5 minutes. The supernatant was decanted. The precipitate was washed with water until the filtrate became neutral, then washed with acetone for several times and dried naturally to obtain the product. The molar ratio among the components in the product determined by XRF method was Cu:V:P=1:0.02:0.2. The amount of element B was less than the lowest detection limit of the XRF method and thus not detected.

An X-ray powder diffractometer was used to analyze the obtained product by XRD. The resultant XRD spectrum showed that only a broad diffuse peak at 2θ=42° was present (the resultant XRD spectrum being similar to FIG. 1 (1)) which is the typical characteristic of an amorphous alloy. Therefore, the resultant Cu—V—P alloy product was an alloy in an amorphous form.

2. Preparing the ZSM-5 Molecular Sieve Carrier 150 g ZSM-5 molecular sieve (a pilot sample from Sinopec Catalyst Company Jianchang filiale, MFI structure: $Na_2O$<0.2 wt. %, Si/Al ratio=40) and 80 g $Ga_2O_3$ (analytical purity, Zibo Rongruida Micro Materials Plant) were mixed homogeneously, and 500 mL solution of 0.07 mol/L $Mg(NO_3)_2$ (analytical purity, Beijing Chemical Works) was added therein. The mixture was heated to 80° C. and stirred for 1 hr. The resultant precipitate was filtered and then washed with distilled water repeatedly until the filtrate became neutral. The precipitate was dried at 110° C. and then calcined at 550° C. for 2 hrs, to obtain a carrier loaded with MgO. Said carrier comprised MgO 1 wt. %, ZSM-5 molecular sieve 64.57 wt. %, and $Ga_2O_3$ 34.43 wt. %.

3. Compounding the Catalyst

The amorphous alloy obtained in above steps, the carrier obtained in above steps, and another carrier ZnO were mixed mechanically in a weight ratio of 3:3:4, tableted, pulverized and screened to particles having sizes of from 20 to 40 meshes. A catalyst was obtained which composition was shown in Table 1.

Example 4

1. Preparing the Amorphous Alloy 11 mL solution of 4.5 mol/L $CuSO_4$, 200 mL solution of 0.05 mol/L $Ce(NO_3)_3$ (analytical purity, Xiaxian Yunli Chemical Co. Ltd., Shangxi Province, China) and 2 g citric acid (industrial grade) were mixed, stirred sufficiently, and then 10 mL 5.0 mol/L $KBH_4$ was added dropwise. The reaction proceeded rapidly to form a black precipitate. The supernatant was decanted. The precipitate was washed with water until the filtrate became neutral, then washed with acetone for several times and dried naturally to obtain the product. The molar ratio among the components in the product determined by XRF method was Cu:Ce:B=1:0.2:1.

An X-ray powder diffractometer was used to analyze the obtained product by XRD. The resultant XRD spectrum showed that only a broad diffuse peak at $2\theta=42°$ was present (the resultant XRD spectrum being similar to FIG. 1 (1)) which is the typical characteristic of an amorphous alloy. Therefore, the resultant Cu—Ce—B alloy product was an alloy in an amorphous form.

2. Preparing the $\gamma$-$Al_2O_3$ Carrier with an Adjuvant 48.6 g $\gamma$-$Al_2O_3$ (a sample from Sinopec Catalyst Company Jianchang filiale) was impregnated in 40 g solution of 52.5 wt. % $Zn(NO_3)_2$ (analytical purity, Beijing Chemical Works, the same below). The mixture was heated to 60° C. for 8 hrs aging, subsequently dried at 110° C., and then calcined at 550° C. for 2 hrs, to obtain $\gamma$-$Al_2O_3$ carrier loaded with ZnO. 10 g $Ag_2O$ (analytical purity, Shanghai Reagent Co., Ltd.) and the $\gamma$-$Al_2O_3$ carrier loaded with ZnO were mixed mechanically to obtain a solid mixture.

5 g $La(NO_3)_3$ was formulated into 28 g solution in a concentration of 22 wt. %. The $La(NO_3)_3$ solution was impregnated onto the above obtained solid mixture by an isovolumetric impregnation method. The impregnated solid mixture was heated to 60° C. for 8 hrs aging, dried at 110° C., and then calcined at 550° C. for 2 hrs, to obtain the $\gamma$-$Al_2O_3$ carrier with the adjuvant. The carrier contained $\gamma$-$Al_2O_3$ 70.7 wt. %, adjuvant ZnO 13.1 wt. %, $Ag_2O$ 14.5 wt. %, and adjuvant $La_2O_3$ 1.6 wt. %.

3. Compounding the Catalyst

The amorphous alloy and carrier obtained in above steps were mixed mechanically in a weight ratio of 1:1, tableted, pulverized and screened to particles having sizes of from 20 to 40 meshes. A catalyst was obtained which composition was shown in Table 1.

Example 5

1. Preparing the Carrier of Mixed Oxides Loaded with $K_2O$ 130 g $MnO_2$ (industrial purity) and 22 g $SnO_2$ (industrial purity, the same below) were impregnated with 333 mL solution of 0.03 mol/L $KNO_3$ (analytical purity, Beijing Chemical Works) by an isovolumetric impregnation method, and then heated to 60° C. for 8 hrs aging, dried at 110° C., calcined at 850° C. for 2 hrs to obtain a carrier of mixed oxides loaded with $K_2O$, wherein the amount of $MnO_2$ was 84.97 wt. %, the amount of $SnO_2$ was 14.38 wt. %, and the amount of adjuvant $K_2O$ was 0.65 wt. %.

2. Preparing the Catalyst 146.24 g carrier obtained as above was added into 100 mL deionized water. The reaction was stirred continuously to form a suspension, 20 mL solution of 2 mol/L $Fe(NO_3)_3$ and 100 mL solution of 4 mol/L $SnCl_2$ (analytical purity, Liaoyang Dingxin Chemical Engineering Co. Ltd., China) were added therein and stirred sufficiently, and then 10 mL 0.5 mol/L $KBH_4$ was added dropwise to obtain a mixed liquor. NaOH was added into 30 mL solution of 3.0 mol/L $KH_2PO_2$ to adjust the pH to 11, and then the solution was added to the above-mentioned mixed liquor. Fe and Sn ions were reduced and simultaneously slowly separated out on the carrier surface, and finally deposited with the reducing agents B and P atoms on the carrier surface to form a black precipitate. After the reaction was complete, the supernatant was decanted, and the precipitate was washed with water until the filtrate became neutral, then washed with acetone for several times and dried naturally to deposit the alloy product on the carrier. The molar ratio among the components in the alloy product determined by XRF method was Fe:Sn:P:B=1:10:2.25:0.125, and the weight ratio between the alloy product and the carrier was 3:7.

Figure 2:
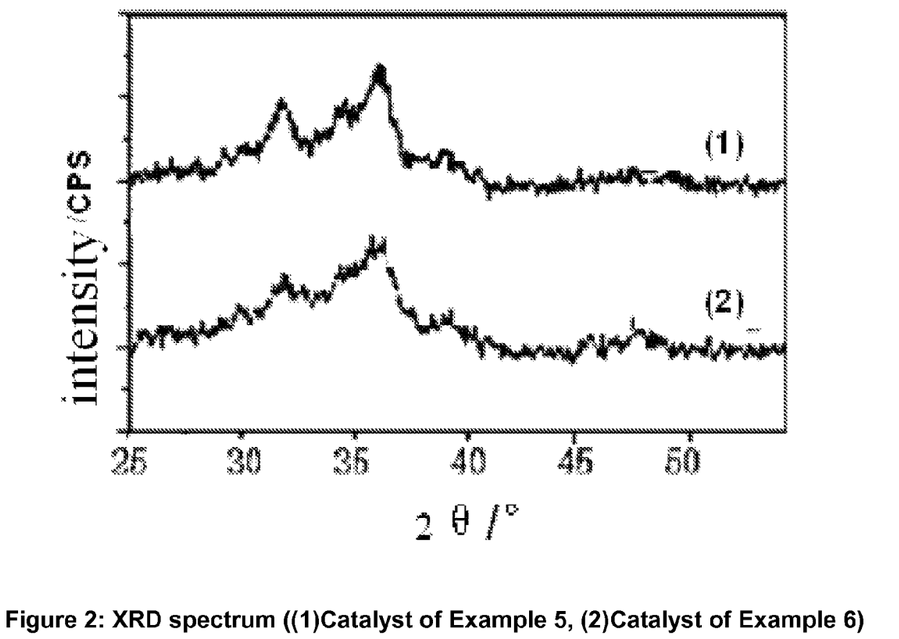

An X-ray powder diffractometer was used to analyze the obtained product deposited on the carrier by XRD. The resultant XRD spectrum showed that only a broad diffuse peak was present (FIG. 2 (1)) which is the typical characteristic of an amorphous alloy. Therefore, the resultant Fe—Sn—P—B alloy product was an alloy in an amorphous form.

The carrier onto which the amorphous alloy was deposited was tableted, pulverized and screened to particles having sizes of from 20 to 40 meshes. A catalyst was obtained which composition was shown in Table 1.

Example 6

1. Preparing the Carrier of Mixed Oxides Loaded with $ZrO_2$ 60 g $MnO_2$ (industrial purity), 60 g active carbon, and 20 g SnO were mixed homogenously, and then impregnated with 300 mL solution of 0.2 mol/L $ZrOCl_2$ by an isovolumetric impregnation method. The mixture was heated to 60° C. for 8 hrs aging, dried at 130° C., calcined at 350° C. for 7 hrs to obtain a carrier of mixed oxides loaded with $ZrO_2$.

2. Preparing the Catalyst 1.97 g above-mentioned carrier was added to 100 mL deionized water. The reaction was stirred continuously to form a suspension. 200 mL solution of 0.4 mol/L $Fe(NO_3)_3$ and 20 mL solution of 0.2 mol/L $ZrOCl_2$ were added into the suspension and stirred sufficiently, and then 20 mL solution of 0.5 mol/L $KBH_4$ was added dropwise to obtain a mixed liquor. NaOH was added into 30 mL solution of 3.0 mol/L $NaH_2PO_2$ to adjust the pH to 9, and then the solution was added to the mixed liquor. Fe and Zr ions were reduced and simultaneously slowly separated out on the carrier surface, and finally deposited with the reducing agents B and P atoms on the carrier surface to form a black precipitate. After the reaction was complete, the supernatant was decanted, and the precipitate was washed with water until the filtrate became neutral, then washed with acetone for several times and dried naturally to deposit the alloy product on the carrier. The molar ratio among the components in the alloy product determined by XRF method was Fe:Zr:P:B=1:0.05:1.125:0.125, and the weight ratio between the alloy product and the carrier was 9:1.

An X-ray powder diffractometer was used to analyze the obtained product deposited on the carrier by XRD. The resultant XRD spectrum showed that only a broad diffuse peak was present (FIG. 2 (2)) which is the typical characteristic of an amorphous alloy. Therefore, the resultant Fe—Zr—P—B alloy product was an alloy in an amorphous form.

The carrier onto which the amorphous alloy was deposited was tabletted, pulverized and screened to particles having sizes of from 20 to 40 meshes. A catalyst was obtained which composition was shown in Table 1.

Example 7

Preparing the Catalyst

By an isovolumetric impregnation method, 60 g $SiO_2$ (macroporous silica gel) was impregnated in 60 mL solution of 2.5 mol/L $KBH_4$, filtered, dried under vacuum at 50° C. for 8 hrs, and then a mixed solution consisting of 50 mL solution of 0.5 mol/L $Fe(NO_3)_3$ and 20 mL solution of 0.5 mol/L $Ni(NO_3)_2$ (analytical purity, Xiaxian Yunli Chemical Co. Ltd., Shangxi Province, China) was added dropwise therein under stirring in ice-water bath and reacted for 1 hr. After the reaction was complete, it was further stirred for 15 minutes, filtered and then dried under vacuum at 120° C. for 2 hrs. Finally, the alloy product was deposited on the carrier. The molar ratio among the components in the alloy product determined by XRF method was Fe:Ni:B=1:0.4:6, and the weight ratio between the alloy product and the carrier was 1:17.24.

Figure 3:
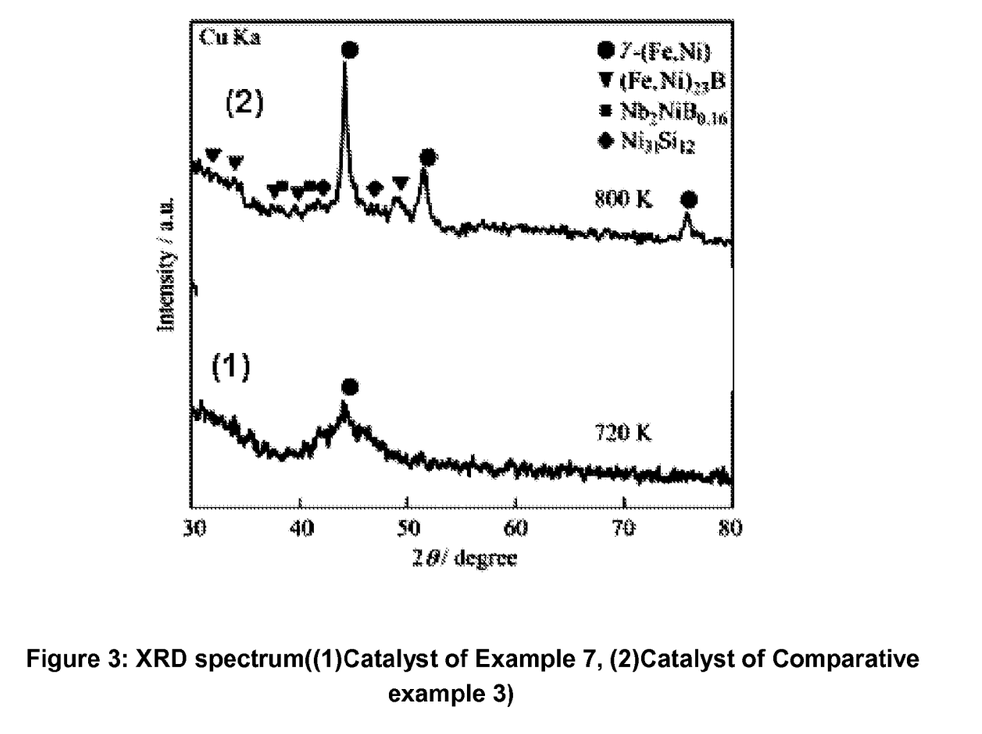

An X-ray powder diffractometer was used to analyze the obtained alloy product deposited on the carrier by XRD. The resultant XRD spectrum showed that only a broad diffuse peak was present (FIG. 3 (1)) which is the typical characteristic of an amorphous alloy. Therefore, the resultant Fe—Ni—B alloy product was an alloy in an amorphous form.

The carrier onto which the amorphous alloy was deposited was tabletted, pulverized and screened to particles having sizes of from 20 to 40 meshes. A catalyst was obtained which composition was shown in Table 1.

Example 8

Preparing the Catalyst 17 mL solution of 3.0 mol/L $KH_2PO_2$ and 17 mL solution of 3.0 mol/L $KBH_4$ were mixed and then NaOH was added therein to adjust the pH to 11 to obtain a solution of mixed reducing agents. By an isovolumetric impregnation method, 60 g carbon powders were impregnated in the solution of mixed reducing agents, filtered, and dried under vacuum at 110° C. for 3 hrs. The treated carbon powders were impregnated in 30 mL solution of 0.01 mol/L $NaBH_4$ by an isovolumetric impregnation method, filtered after the impregnation being complete, dried under vacuum at 70° C. for 4 hrs to obtain the impregnated and dried carbon powder. A mixed solution consisting of 5 mL solution of 0.5 mol/L ammonium molybdate (analytical purity, Kunshan Xingbang W&M Technology Co., Ltd.), 2 mL solution of 0.5 mol/L $Co(NO_3)_2$ (analytical purity, Xiaxian Yunli Chemical Co. Ltd., Shangxi Province, China) and 40 mL solution of 0.5 mol/L $Cu(NO_3)_2$ (analytical purity, Zibo Rongruida Micro Materials Plant) was added dropwise into the impregnated and dried carbon powder under stirring in an ice-water bath and reacted for 1 hr. After the reaction was complete, it was further stirred for 15 minutes, filtered and then dried under vacuum at 120° C. for 2 hrs. Finally, the alloy product was deposited on the carrier. The molar ratio among the components in the alloy product determined by XRF method was Cu:Mo:Co:P:B=1:0.125: 0.05:2.55:2.565, and the weight ratio between the alloy product and the carrier was 1:6.39.

An X-ray powder diffractometer was used to analyze the obtained alloy product deposited on the carrier by XRD. The resultant XRD spectrum showed that only a broad diffuse peak at 2θ=42° was present (the resultant XRD spectrum was similar to FIG. 1 (1)) which is the typical characteristic of an amorphous alloy. Therefore, the resultant Cu—Mo—Co—P—B alloy product was an alloy in an amorphous form.

The carrier onto which the amorphous alloy was deposited was tabletted, pulverized and screened to particles having sizes of from 20 to 40 meshes. A catalyst was obtained which composition was shown in Table 1.

Example 9

Preparing the Carrier Loaded with the Amorphous Alloy 10 g active carbon, 10 g CoO (industrial purity) and 5 g $SiO_2$ were mixed homogeneously and added into 200 mL deionized water under continuously stirring, and then 100 mL solution of 0.4 mol/L $Fe(NO_3)_3$, 30 mL solution of 0.05 mol/L $La(NO_3)_3$ (analytical purity, Zibo Rongruida Micro Materials Plant), and 2 g citric acid (industrial grade) were added therein and stirred sufficiently to form a suspension. To 50 mL solution of 1.1 mol/L $KBH_4$ was added NaOH to adjust the pH to 7, and then the solution was added dropwise to the suspension. Fe and La ions were reduced and simultaneously slowly separated out on the carrier surface, and finally deposited with the reducing agent B atom on the carrier surface to form a black precipitate. The supernatant was decanted, the precipitate was washed with water until the filtrate became neutral, then washed with acetone for several times and dried naturally to finally deposit the alloy product on the carrier. The molar ratio among the components in the alloy product determined by XRF method was Fe:La:B=1:0.04:1.37, and the amount of the amorphous alloy in the alloy product was 10.1 wt. %.

An X-ray powder diffractometer was used to analyze the obtained product deposited on the carrier by XRD. The resultant XRD spectrum showed that only a broad diffuse peak was present (the resultant XRD spectrum was similar to FIG. 2 (2)) which is the typical characteristic of an amorphous alloy. Therefore, the resultant Fe—La—B alloy product was an alloy in an amorphous form.

2. Compounding the Catalyst

The carrier onto which the amorphous alloy was loaded was mixed mechanically with SAPO-34 molecular sieve (a pilot sample from Sinopec Catalyst Company Jianchang filiale, CHA structure: $Na_2O$<0.2 wt. %, Si/Al ratio=13) carrier were mixed mechanically in a weight ratio of 7:3, tabletted, pulverized and screened to particles having sizes of from 20 to 40 meshes. A catalyst was obtained which composition was shown in Table 1.

Example 10

Preparing the Catalyst 3.75 g ZnO and 0.9 g $V_2O_5$ (analytical purity, Wuhu Renben Alloy Co., Ltd) were added into 100 mL deionized water and stirred continuously, and then 100 mL solution of 0.5 mol/L $CuSO_4$, 200 mL solution of 0.025 mol/L $Zn(NO_3)_4$ (analytical purity, Xiaxian Yunli Chemical Co. Ltd., Shangxi Province, China), 400 mL solution of 0.025 mol/L $Cr(NO_3)_3$ (analytical purity, Xiaxian Yunli Chemical Co. Ltd., Shangxi Province, China), and 2 g citric acid (industrial grade) were added therein and stirred sufficiently to form a suspension. To 50 mL solution of 1.0 mol/L $KBH_4$ was added NaOH to adjust the pH to 7, and then the solution was added dropwise to the suspension. Cu, Zn, and Cr ions were reduced and simultaneously slowly separated out on the carrier surface, and finally deposited with the reducing agent B atom on the carrier surface to form a black precipitate. The supernatant was decanted, the precipitate was washed with water until the filtrate became neutral, then washed with acetone for several times and dried naturally to finally deposit the alloy product on the carrier. The molar ratio among the components in the alloy product determined by XRF method was Cu:Zn:Cr:B=1:0.1:2:1, and the weight ratio between the alloy product and the carrier was 7:3.

An X-ray powder diffractometer was used to analyze the obtained alloy product deposited on the carrier by XRD. The resultant XRD spectrum showed that only a broad diffuse peak at $2\theta=42°$ was present (the resultant XRD spectrum was similar to FIG. 1 (1)) which is the typical characteristic of an amorphous alloy. Therefore, the resultant Cu—Zn—Cr—B alloy product was an alloy in an amorphous form.

The carrier onto which the amorphous alloy was deposited was tableted, pulverized and screened to particles having sizes of from 20 to 40 meshes. A catalyst was obtained which composition was shown in Table 1.

Comparative Examples

Comparative Example 1

1. Preparing the Amorphous Alloy

To 300 mL solution of 0.5 mol/L $CuSO_4$ was added 5 g citric acid as complexing agent, and added 30 mL solution of 0.05 mol/L $La(NO_3)_3$, the mixture was stirred sufficiently, to which 30 mL solution of 0.5 mol/L $KBH_4$ was poured, and the reaction was stirred rapidly. A black precipitate was formed rapidly, the supernatant was decanted, the precipitate was washed with water until the filtrate became neutral, then washed with acetone for several times and dried naturally to obtain the product. The molar ratio among the components in the product determined by XRF method was Cu:La:B=1:0.01:0.1.

The resultant Cu—La—B alloy product was calcined under nitrogen gas at 600° C. for 4 hrs to obtain crystalline alloy powder. An X-ray powder diffractometer (D/MAX-2500 type X-ray diffractometer from Rigaku Cooperation, Cu K$\alpha$ ray, a current of 100 mA, the same below) was used to analyze the obtained powder by XRD. The resultant XRD spectrum showed that a sharp peak at $2\theta=42°$ was present (FIG. 1 (2)). Therefore, the resultant Cu—La—B alloy product was an alloy in a crystalline form.

2. Preparing the Carrier of Mixed Oxides 60 g ZnO, 20 g $SiO_2$ and 200 g distilled water were mixed, 130 g aqueous solution of 20 wt. % $ZrOCl_2.8H_2O$, 5 g $MnO_2$ (industrial purity), 49 g aqueous solution of 20 wt. % $CaCl_2$ (industrial purity) and 10 g aqueous solution of 1 wt. % HCl were simultaneously added dropwise under strongly stirring,

TABLE 1

| Example No. | Composition of the amorphous alloy (molar ratio) | Carrier composition (wt.) | The method of introduction of the adjuvant | wt. % of the amorphous alloy in the catalyst |
|---|---|---|---|---|
| 1 | Cu:Ga:B = 1:0.01:0.1 | $ZrO_2$ (10%), ZnO (60%), CaO (5%) $SiO_2$ (20%), $MnO_2$ (5%) | Precipitation | 40 |
| 2 | Cu:Mn:P:B = 1:0.52:2:4 | $FeCl_3$ (5%), $SnCl_4$ (5%), ZnO (30%), active carbon (60%) | Kneading | 23 |
| 3 | Cu:V:P = 1:0.02:0.2 | ZSM-5 molecular sieve (64.57%), MgO (1%), $Ga_2O_3$ (34.43%) | Ion exchange | 30 |
| 4 | Cu:Ce:B = 1:0.2:1 | $\gamma$-$Al_2O_3$ (70.7%), ZnO (13.1%) $Ag_2O$ (14.5%), $La_2O_3$ (1.6%) | Impregnation | 50 |
| 5 | Fe:Sn:P:B = 1:10:2.25:0.125 | $K_2O$ (0.65%), $MnO_2$ (84.97%), $SnO_2$ (14.38%) | Impregnation | 30 |
| 6 | Fe:Zr:P:B = 1:0.05:1.125:0.125 | $ZrO_2$ (5.01%), $MnO_2$ (40.71%), $SnO_2$ (13.57%), active carbon (40.71%) | Impregnation | 90 |
| 7 | Fe:Ni:B = 1:0.4:6 | $SiO_2$ | Impregnation | 5.5 |
| 8 | Cu:Mo:Co:P:B = 1:0.125:0.05:2.55:2.565 | Carbon powder | Impregnation | 13.52 |
| 9 | Fe:La:B = 1:0.04:1.37 | Active carbon (27.09%), $SiO_2$ (13.55%), SAPO-34 molecular sieve (32.27%), CoO (27.09%) | Not modified | 7.07 |
| 10 | Cu:Zn:Cr:B = 1:0.1:2:1 | ZnO (80.65%), $V_2O_5$ (19.35%) | Not modified | 70 | then 50 g aqueous solution of 5 wt. % sodium carbonate was added dropwise. After the addition was complete, the mixture was stirred for further 1 hr, the resultant precipitate was filtered and washed with distilled water repeatedly until there was no Cl$^-$, the precipitate was dried at 110° C. and then calcined at 550° C. for 2 hrs to obtain 100 g carrier comprising ZnO 60 wt. %, SiO$_2$ 20 wt. %, ZrO$_2$ 10 wt. %, adjuvant MnO$_2$ 5 wt. %, and adjuvant CaO 5 wt. %.

3. Compounding the Catalyst

The crystalline alloy and carrier were mixed mechanically in a weight ratio of 2:3, tabletted, pulverized and screened to particles having sizes of from 20 to 40 meshes to obtain a catalyst.

Comparative Example 2

A catalyst containing crystalline Cu and Ga was prepared by the follow method.

70 g SiO$_2$ was impregnated with 40 g aqueous solution of 62.5 wt. % Cu(NO$_3$)$_2$ (analytical purity, Zibo Rongruida Micro Materials Plant), dried at 80° C. for 6 hrs, 120° C. for 4 hrs, and then calcined at 550° C. for 2 hrs to obtain CuO—SiO$_2$ complex.

The resultant CuO—SiO$_2$ complex was impregnated with 40 g aqueous solution of 0.85 wt. % Ga(NO$_3$)$_3$, dried at 80° C. for 6 hrs, 120° C. for 4 hrs, and then calcined at 550° C. for 2 hrs to obtain Ga$_2$O$_3$—CuO—SiO$_2$ complex. The molar ratio among the components in the alloy product determined by XRF method was Cu:Ga=1:0.01. The XRD spectrum of the alloy product was shown by FIG. 1(3) which showed that a sharp peak was present. Therefore, the resultant alloy product was an alloy in a crystalline form.

60 g ZnO (industrial purity, the same below), 20 g SiO$_2$ and 200 g distilled water were mixed, 130 g aqueous solution of 20 wt. % ZrOCl$_2$.8H$_2$O, 5 g MnO$_2$ (industrial purity), 49 g aqueous solution of 20 wt. % CaCl$_2$ (industrial purity) and 10 g aqueous solution of 1 wt. % HCl were simultaneously added dropwise under strongly stirring, then 50 g aqueous solution of 5 wt. % sodium carbonate was added dropwise. After the addition was complete, the mixture was stirred for further 1 hr, the resultant precipitate was filtered and washed with distilled water repeatedly until there was no Cl$^-$, the precipitate was dried at 110° C. and then calcined at 550° C. for 2 hrs to obtain 100 g carrier comprising ZnO 60 wt. %, SiO$_2$ 20 wt. %, ZrO$_2$ 10 wt. %, adjuvant MnO$_2$ 5 wt. %, and adjuvant CaO 5 wt. %.

The crystalline alloy and carrier were mixed mechanically in a weight ratio of 2:3, tabletted, pulverized and screened to particles having sizes of from 20 to 40 meshes to obtain a catalyst.

Comparative Example 3

Preparing the Catalyst

By an isovolumetric impregnation method, 60 g SiO$_2$ (macroporous silica gel) was impregnated in 60 mL solution of 2.5 mol/L KBH$_4$, filtered, dried under vacuum at 50° C. for 8 hrs, and then a mixed solution consisting of 50 mL solution of 0.5 mol/L Fe(NO$_3$)$_3$ and 20 mL solution of 0.5 mol/L Ni(NO$_3$)$_2$ was added dropwise therein under stirring in an ice-water bath and reacted for 1 hr. After the reaction was complete, it was further stirred for 15 minutes, filtered and then dried under vacuum at 120° C. for 2 hrs. Finally, the alloy product was deposited on the carrier. The molar ratio among the components in the alloy product determined by XRF method was Fe:Ni:B=1:0.4:6, and the weight ratio between the alloy product and the carrier was 1:17.24. The carrier onto which the amorphous alloy was deposited was tabletted, pulverized and screened to particles having sizes of from 20 to 40 meshes to obtain a catalyst. The catalyst was calcined under nitrogen gas at 600° C. for 4 hrs to obtain crystalline powder. An X-ray powder diffractometer (D/MAX-2500 type X-ray diffractometer from Rigaku Cooperation, Cu Kα ray, a current of 100 mA, the same below) was used to analyze the obtained powder by XRD. The resultant XRD spectrum showed that a sharp peak at 2θ=42° was present (FIG. 3 (3)). Therefore, the resultant Fe—Ni—B alloy product was an alloy in a crystalline form.

Example 11

The process for preparing methanol, dimethyl ether, and low carbon olefins from syngas was carried out by means of each catalyst prepared from Examples 1-10 and Comparative Examples 1-3.

The gas phase reaction was carried out in a pressurized reaction evaluation apparatus of continuous flow fixed bed reactor.

1.5 g of catalyst was loaded into the reactor. Prior to the reaction, the reactor containing the catalyst was purged with a reductive gas for 0.5 hr. Subsequently, the reaction temperature was adjusted, and syngas was fed into the reactor in a feed space velocity. The composition of the reductive gas, purge temperature, operation conditions and composition of the feedstock syngas were listed in Table 2. A sample was taken for analysis after the reaction proceeded for 3 hrs. Carbon monoxide was on line analyzed by HP 6890 type gas chromatograph, and the products of methanol, dimethyl ether and low carbon olefins were analyzed by PORAPAK-N chromatographic column.

In order to compare Example 1 with Comparative Examples 1-2, and Example 7 with Comparative Example 3, Example 1 and Comparative Examples 1-2 shared the substantially same operation conditions and feedstock syngas composition, and Example 7 and Comparative Example 3 shared too.

TABLE 2

| Catalyst No. | Composition of the reductive gas (wt. %) | Purge temperature/ ° C. | Feed space velocity/ mL/g · h | Reaction pressure/ MPa | Reaction temperature/ ° C. | Composition of the feedstock gas (wt. %) |
| --- | --- | --- | --- | --- | --- | --- |
| Example 1 | 5% H$_2$, 95% N$_2$ | 130 | 1000 | 4 | 230 | 31% CO, 6% CO$_2$, 63% H$_2$ |
| Comparative Example 1 | 5% H$_2$, 95% N$_2$ | 130 | 1000 | 4 | 230 | 31% CO, 6% CO$_2$, 63% H$_2$ |

TABLE 2-continued

| Catalyst No. | Composition of the reductive gas (wt. %) | Purge temperature/ °C. | Feed space velocity/ mL/g · h | Reaction pressure/ MPa | Reaction temperature/ °C. | Composition of the feedstock gas (wt. %) |
|---|---|---|---|---|---|---|
| Comparative Example 2 | 5% $H_2$, 95% $N_2$ | 130 | 1000 | 4 | 230 | 31% CO, 6% $CO_2$, 63% $H_2$ |
| Example 2 | 1% $H_2$, 99% $N_2$ | 600 | 1500 | 4 | 250 | 31% CO, 6% $CO_2$, 63% $H_2$ |
| Example 3 | 5% $H_2$, 95% He | 300 | 1500 | 4 | 270 | 31% CO, 6% $CO_2$, 63% $H_2$ |
| Example 4 | 5% $H_2$, 95% $N_2$ | 240 | 1000 | 6 | 200 | 31% CO, 6% $CO_2$, 63% $H_2$ |
| Example 5 | 5% $H_2$, 95% Ar | 400 | 5000 | 4 | 270 | 42% CO, 8% $CO_2$, 50% $H_2$ |
| Example 6 | 5% $H_2$, 80% $N_2$, 15% Ar | 300 | 1500 | 1 | 290 | 42% CO, 8% $CO_2$, 50% $H_2$ |
| Example 7 | 10% $H_2$, 90% $N_2$ | 280 | 2700 | 2 | 270 | 26% CO, 2% $CO_2$, 72% $H_2$ |
| Comparative Example 3 | 10% $H_2$, 90% $N_2$ | 280 | 2700 | 2 | 270 | 26% CO, 2% $CO_2$, 72% $H_2$ |
| Example 8 | 5% $H_2$, 75% He, 20% $N_2$ | 400 | 9000 | 1 | 400 | 26% CO, 2% $CO_2$, 72% $H_2$ |
| Example 9 | 5% $H_2$, 95% $N_2$ | 300 | 1500 | 0.5 | 350 | 26% CO, 2% $CO_2$, 72% $H_2$ |
| Example 10 | 5% $H_2$, 95% $N_2$ | 400 | 1500 | 0.5 | 300 | 42% CO, 8% $CO_2$, 50% $H_2$ |

The CO conversion, selectivity of each of methanol, dimethyl ether, ethylene, and propylene, as well as carbon availability during the process for preparing methanol, dimethyl ether, and low carbon olefins from syngas were calculated by the following equations and the results were shown in Table 3.

CO conversion(%)=moles of CO consumed by the reaction/moles of CO fed into the reaction Dimethyl ether selectivity(%)=moles of dimethyl ether produced by the reaction/moles of CO consumed by the reaction Methanol selectivity(%)=moles of methanol produced by the reaction/moles of CO consumed by the reaction Ethylene selectivity(%)=(moles of ethylene produced by the reaction×2)/moles of CO consumed by the reaction Propylene selectivity(%)=(moles of propylene produced by the reaction×3)/moles of CO consumed by the reaction Carbon availability(%)=(moles of CO consumed by the reaction−moles of CO produced by the reaction)/moles of CO fed into the reaction

TABLE 3

| Catalyst | CO conversion (%) | Dimethyl ether selectivity (%) | Methanol selectivity (%) | Ethylene selectivity (%) | Propylene selectivity (%) | Carbon availability (%) |
|---|---|---|---|---|---|---|
| Example 1 | 85 | 92 | 3 | 1.5 | 1.5 | 63 |
| Comparative Example 1 | 70 | 72 | 23 | 1.4 | 1 | 59 |
| Comparative Example 2 | 65 | 73 | 20 | 1.3 | 1 | 50 |
| Example 2 | 90 | 94 | 2 | 1.9 | 1.6 | 64 |
| Example 3 | 90 | 95 | 2 | 2.1 | 1.7 | 64 |
| Example 4 | 95 | 91 | 4 | 0.7 | 1 | 69 |
| Example 5 | 93 | 92 | 2 | 2.3 | 1.7 | 66 |
| Example 6 | 94 | 3 | 0.1 | 17 | 24 | 67 |
| Example 7 | 96 | 4 | 0.2 | 21 | 33 | 72 |
| Comparative Example 3 | 85 | 10 | 7 | 15 | 20 | 60 |
| Example 8 | 92 | 2 | 0.5 | 19 | 28 | 67 |
| Example 9 | 93 | 3 | 0.4 | 17 | 26 | 68 |
| Example 10 | 91 | 2 | 0.4 | 20 | 30 | 65 |

It can be seen from Table 3, in the process for preparing methanol, dimethyl ether, and low carbon olefins from syngas, the catalysts according to the present invention can achieve a high CO conversion, a high selectivity of the target product, and high carbon availability.

We claim:

1. A process for co-producing methanol, dimethyl ether, and low carbon olefins from syngas, wherein the process comprises the step of contacting syngas with a catalyst under the conditions for converting the syngas into methanol, dimethyl ether, and low carbon olefins, characterized in that, the catalyst contains an amorphous alloy expressed as M-X wherein X represents B, P, or a combination thereof, M represents two or more metals selected from Groups IIIA, IVA, VA, IB, IIB, IVB, VB, VIB, VIIB, VIII and Lanthanide series of the Periodic Table of Elements.

2. The process according to claim 1, wherein the molar ratio between M and X in the alloy is from 0.01 to 15.

3. The process according to claim 1, wherein the molar ratio between M and X in the alloy is from 0.2 to 10.

4. The process according to claim 1, wherein M is two or more metals selected from Lanthanide series, and the third, fourth and fifth rows of Group IIIA, IVA, VA, IB, IIB, IVB, VB, VIB, VIIB, and VIII of the Periodic Table of Elements.

5. The process according to claim 1, wherein M is two or more metals selected from Cu, Zn, V, Cr, Mn, Fe, Co, Ni, Zr, Mo, Sn, and La.

6. The process according to claim 1, wherein said M comprises Cu.

7. The process according to claim 1, wherein said M comprises Cu and Zn.

8. The process according to claim 1, wherein said catalyst further comprises a carrier into or onto which the amorphous alloy is dispersed or loaded, and based on the total weight of the catalyst, the amount of the amorphous alloy is 3-90 wt. %, and the amount of the carrier is 10-97 wt. %.

9. The process according to claim 8, wherein said carrier is one or more substances selected from non-oxidative porous inorganic oxides, molecular sieves, active carbons, clays, phosphates, sulfates, and metal halides.

10. The process according to claim 8, wherein said catalyst further contains an adjuvant which is loaded on/in the carrier and selected from one or more elements or oxides thereof of Group IA, IIA, IIIA, IVA, VA, IB, IIB, IVB, VIII, and Lanthanide series of the Periodic Table of Elements.

11. The process according to claim 10, wherein, based on the weight of the carrier, the amount of the adjuvant is 0.5-40 wt. %.

12. The process according to claim 10, wherein said adjuvant is one or more elements or oxides thereof selected from Lanthanide series, and the third, fourth and fifth rows of Group IA, IIA, IIIA, IVA, VA, IB, IIB, IVB, and VIII of the Periodic Table of Elements.

13. The process according to claim 10, wherein said adjuvant is one or more elements or oxides thereof selected from K, Ca, Mg, Ga, Sn, P, Cu, Zn, Zr, Fe, and La.

14. The process according to claim 1, wherein the conditions for converting the syngas into methanol, dimethyl ether, and low carbon olefins include a reaction temperature of 200-400° C., a reaction pressure of 0.5-6 MPa, a space velocity of the syngas feed of 1000-10000 mL/g·h, and a molar ratio between $H_2$ and CO in the syngas from 1 to 3.

15. The process according to claim 14, wherein the reaction temperature is 200-270° C., and the reaction pressure is 1-6 MPa, whereas methanol and dimethyl ether are produced as the main products, and the low carbon olefins are produced as the byproducts.

16. The process according to claim 14, wherein the reaction temperature is 270-400° C., and the reaction pressure is 0.5-2 MPa, whereas the low carbon olefins are produced as the main products, and methanol and dimethyl ether are produced as the byproducts.

17. The process according to claim 8, wherein the catalyst is prepared by mechanically mixing the amorphous alloy and the carrier; using an impregnation-reduction or reduction-impregnation method to directly impregnate the amorphous alloy onto the carrier; or using a co-precipitation method to directly deposit the amorphous alloy onto the carrier; or any combination of above methods.

* * * * *